United States Patent [19]

Grodberg

[11] Patent Number: 4,861,590
[45] Date of Patent: Aug. 29, 1989

[54] SUSTAINED RELEASE FLUORIDE AND CALCIUM COMPOSITION

[75] Inventor: Marcus G. Grodberg, Newton, Mass.

[73] Assignee: Colgate-Palmolive Company, New York, N.Y.

[21] Appl. No.: 911,686

[22] Filed: Sep. 25, 1986

[51] Int. Cl.$^4$ .......................... A61K 9/22; A61K 9/26; A61K 33/16
[52] U.S. Cl. ..................................... 424/602; 424/468; 424/469; 424/606; 424/687
[58] Field of Search .................. 424/52, 151, 468, 469

[56] References Cited

U.S. PATENT DOCUMENTS

| | | | |
|---|---|---|---|
| 2,449,184 | 9/1948 | Strean | 424/52 |
| 2,700,012 | 1/1955 | Merckel et al. | 424/52 |
| 2,967,131 | 1/1961 | Elbreder et al. | 424/151 |
| 3,119,743 | 1/1964 | Ericsson | 424/52 |
| 3,312,594 | 4/1967 | Cyr et al. | 424/151 |
| 3,431,339 | 3/1969 | Gyarmathy et al. | 424/57 |
| 4,169,885 | 10/1979 | Raaf et al. | 424/151 |
| 4,265,877 | 5/1981 | Tenta | 424/151 |
| 4,726,952 | 2/1988 | Walsdorf et al. | 424/151 |

FOREIGN PATENT DOCUMENTS

| | | | |
|---|---|---|---|
| 3127984 | 2/1983 | Fed. Rep. of Germany | 424/151 |
| 2497665 | 7/1982 | France | 424/151 |
| 1221633 | 2/1971 | United Kingdom . | |

OTHER PUBLICATIONS

Eisch, C.A. 89:12151a (1978).
Jowsey, C.A. 89:122856s (1978).
Becker, C.A. 90:132993u (1979).
Ericksson, C.A. 90:180340a (1979).
Fuchs, C.A. 91:186370c (1979).
White, C.A. 99:200373e (1983).
Baylink, C.A. 99:205397a (1983).
Anderson, C.A. 104:45750e, 45761F (1986).

*Primary Examiner*—Shep K. Rose
*Attorney, Agent, or Firm*—Norman Blumenkopf; Murray M. Grill

[57] ABSTRACT

A slow release tablet or the like for releasing fluoride and calcium ions in a manner so as to reduce the formation of calcium fluoride and to reduce gastrointestinal discomfort comprising the use of MFP together with a calcium-containing composition.

1 Claim, No Drawings

SUSTAINED RELEASE FLUORIDE AND CALCIUM COMPOSITION

BACKGROUND OF THE INVENTION

1. Field of the Invention

This invention relates to a sustained release systemic fluoride drug product for treatment or prevention of osteoporosis or other bone disease. More particularly, this invention relates to the use of sodium monofluorophosphate, alone or in combination with another fluorine compound, with a calcium compound in a sustained release solid unit dosage form, suitable for use in the treatment and prevention of osteoporosis, alveolar bone loss or other bone diseases where systemic fluoride ion is efficacious.

2. Description of the Prior Art

Flouride stimulates the activity of bone-forming cells and, together with calcium and phosphate, the two major components of bone, is also stored in the bone structure. Fluoride seems to directly stimulate the proliferation of osteoblasts resulting in an increase in bone formation.

U.S. Pat. No. 3,287,219 discloses the oral administration of sodium fluoride to promote bone healing.

The role of fluoride in strengthening the teeth and in imparting acid resistance and preventing caries in dental treatment is well documented. The use of sodium fluoride tablets and liquids for infants and young children in areas where the drinking water is not or is only insufficiently fluoridated is well known. For this purpose, fluoride ion from NaF is administered in dosages of about 0.25 to about 1 mg per day. Representative patents in this area include U.S. Pat. Nos. 3,306,824, 4,265,877 and 4,397,837 (toothpaste). The use of sodium monofluorophosphate (MFP) in dental products, particularly toothpaste products, as an anticaries fluoride additive is also well known and is mentioned in U.S. Pat. No. 4,397,837 cited above. The MFP is slowly metabolized by an intestinal enzyme, MFPase or alkaline phosphatase into free fluoride ion which, in turn, is absorbed into the blood stream, some of the MFP being directly absorbed in the liver and converted therein to F ion.

More recently, the use of NaF for the treatment of bone disease to promote bone formation and strengthen bone has received wide attention. In fact, although not yet approved for use in the United States, both NaF and MFP products for the treatment and prevention of osteoporosis are available in Europe. Thus, Flurexal ® is an enteric coated tablet containing 22 mg sodium fluoride (10 mg F) sold by Zyma SA Nyon Suisse; Tridin ® is a chewable tablet containing 38 mg sodium monofluorophosphate (5 mg F), 500 mg calcium gluconate monohydrate, 500 mg calcium citrate tetrohydrate, 200 mg carboxymethyl cellulose, available form Opfermann Arzneimittel GmbH.

According to the directions for use provided with the medications, Flurexal ® should be taken three times each day, while Triden ® should be taken 1-2 tablets three times a day for treatment or one tablet three times a day for prevention of steroidosteoporosis. In general, the typical recommended dosage for F ion is in the order of from about 30 to 60 mg per day for a human adult.

The literature provided with Tridin ® states that gastric and intestinal irritation is seldom observed. To the same effect, Yngve Ericson, "Monofluorophosphate Physiology: General Considerations," Caries Res. 17 (Suppl. 1), pages 46–55 (1983) reported that "neither in patients nor in numerous experiments with laboratory workers has any subjective discomfort been recorded with doses up to 30 mg F as MFP." However, in one of the present inventor's own clinical studies the patient evaluations, the occurrence of gastric and intestinal distress was observed in a significant number of cases.

Attempts to solve the adverse side effects of gastrointestinal (GI) tract symptoms by minimizing the availability of F ion in the stomach by providing NaF in a sustained release form have only been partially effective in avoiding GI irrigation. More particularly, it has been observed that, while slow release sodium fluoride is well tolerated by approximately 70% of patients, there is adverse gastro-intestinal effectis in the other approximate 30% of patients. Representative U.S. patents related to the use of treatment of patients with a fluoride composition and with a calcium composition are Pat. Nos. 3,287,219, 4,130,630 and 3,345,265.

SUMMARY OF THE INVENTION

The present invention provides a fluoride and calcium treatment for osteoporosis, alveolar bone disease and other localized bone disorders which virtually solves the problem of gastric irritation.

Quite surprisingly, in view of the fact that the sustained release type unitary dosage product for administering NaF is only variably effective in avoiding the occurrence of gastric irritation, it has now been discovered that, when MFP is administered in a sustained release form, the occurrence of gastric intestinal irritation is almost totally eliminated.

Accordingly, it is an object of this invention to provide a fluoride ion drug preparation with calcium useful in the treatment or prevention of osteoporosis (bone disease) which does not cause adverse GI symptoms, such as gastric irritation.

It is a specific object of this invention to provide a unitary dosage form of MFP with calcium which provides sufficient quantities of F ion to be useful in the prevention or treatment of osteoporosis in which the MFP is administered from the unitary dosage product over the course of at least several hours, preferably a maximum of eight hours, whereby occurrence of gastric irritation is avoided.

It is another object of the invention to provide a method for treating or preventing osteoporosis by administering, at least once daily, to a patient suffering from or at risk of osteoporosis a solid, unitary dosage product containing a sufficient amount of MFP and calcium effective for the promotion of, or maintenance of, formation and strengthening of diseased or weakened bone, wherein the product includes means for slowly releasing the MFP over the course of at least several hours to a maximum of eight hours.

In accordance with these objectives and other objects, which will become apparent from the following description, the present invention provides, in one aspect thereof, a medication for providing fluoride ion and calcium for the treatment or prevention of osteoporosis or other bone disease, including alveolar bone loss, which is in the form of a solid unitary dosage tablet or capsule containing from about 20 milligrams (mg) to about 100 mg of sodium monofluorophosphate ($Na_2PO_3F$), together with a dosage of calcium-containing composition, and further including means for controlling the release of the monofluorophosphate over a period extending up to a maximum of eight hours whereby the quantity of fluoride ion present in the stomach at any given time is below the threshold value at which gastric irritation will occur.

The sustained release unitary dosage product of this invention may include MFP and calcium as the active ingredients. Alternatively, MFP may be used in combination with small amounts of NaF, together with the ionizable calcium compound.

In a specific and preferred embodiment of the invention, the means for controlling release of MFP and any other active ingredient includes a mass of water swellable cellulosic powder forming a coherent fibrous powder network as a matrix in which the monofluorophosphate and calcium compound is uniformly and homogeneously dispersed, whereby, upon introduction of the unitary dosage product into an aqueous medium, the cellulosic fibers at the surface of the product soften and loosen from the remaining mass of fibers to thereby release a stream of the monofluorophosphate and calcium compound.

According to the method aspect of the invention, a patient suffering from or at risk of osteoporosis in treated with at least one of the sustained release unitary dosage MFP and calcium products of this invention.

DETAILED DESCRIPTION OF THE INVENTION

Osteoporosis can be broadly defined as increasing weakness and fragility of the bones. It most frequently occurs in elderly, postmenopausal women and in elderly (presenile or senile) men, but also occurs in idiopathic forms. Osteoporosis can also occur in connection with, i.e. as an undesirable side effect of, corticoid treatment (steriod-osteoporosis). Certain localized forms of bone disease may also be associated with a general weakness and fragility of the bone structure due to insufficient new bone formation. Therapeutic indications include any bone wasting disease, genetic, such as osteogenesis inperfecta, or acquired, such as renal bone disease.

One of the effects of advanced periodontal disease is the loss of alveolar bone (i.e. that portion of the jaw bones that support the teeth) mass, which eventually causes loosening and loss of teeth. Alveolar bone loss may also occur after tooth extractions and, in some cases, after the insertion of dental implants.

Bone is composed of an organic phase (predominently collagen) and an inorganic crystalline phase of calcium phosphate, or more specifically, hydroxyapatite, $Ca_{10}(PO_4)_6(OH)_2$. Fluoride plays an important role in the prevention of bone loss by stimulating the formation of less soluble fluorapatite $Ca_{10}(PO_4)_6F_2$. Therefore, in osteoporosis, alveolar bone loss and other bone diseases associated with general weakening or loss of the bone tissue, or in cases where the normal dietary intake of calcium is insufficient, a dietary supplement to supply additional calcium is usually appropriate. The addition to the calcium supplement of, or the separate administration of, a source of fluoride ion will, according to recent scientific research, greatly enhance the reversal of bone loss, the fluoride stimulating new bone formation and the calcium being an indespensable building block for bone tissue.

Sodium fluoride and sodium monofluorophosphate can each be used to provide the fluoride ion to be absorbed into the blood for eventual skeletal uptake. Sodium fluoride, NaF, has the advantage that it has a higher F content than sodium monofluorophosphate, MFP. NaF is also more rapidly absorbed, at least in the first few hours, into the blood. However, NaF has a higher acute toxicity than MFP and causes stomach irritation in a much higher percentage of patients than does MFP. Moreover, and perhaps most important, is the fact that NaF is incompatible with ionizable calcium compounds, forming insoluble $CaF_2$, thereby depleting the availability of the F ion to a large extent and of the Ca ion to a smaller extent (based on the much greater total quantity of calcium present in the patient's system). On the other hand, MFP is compatible with ionizable calcium compounds since Ca(MFP) is about twenty times more soluble than $CaF_2$.

Unfortunately, when ingested orally in the recommended dosages, typically about 30 to 60 mg F per day for human adults, MFP, although not as pronounced as NaF, also causes stomach irritation.

In accordance with the present invention, it has been found that by incorporating the MFP in conjunction with a calcium mineral supplement and/or in combination with a small amount of sodium fluoride, the occurrence of GI irritation can be avoided. Although not wishing to be bound by any particular theory, it is presumed that by only gradually releasing the MFP from the unitary dosage product, the quantity of fluoride ion present in the stomach at any given time is below the threshold value at which gastrointestinal irritation will occur. Since a similar alleviation of GI symptoms is not observed for a slow release NaF product, it is further presumed that the more rapid ionization of NaF into sodium and fluorine ions, as compared to the rate of enzymatic hydrolysis of MFP in the stomach, may also account for this different result. In any case, by whatever mode of action, by incorporating the MFP with means for controlling the release of the monofluorophosphate over a period extending up to a maximum of eight hours from the time of ingestion, gastrointestinal irritation will be avoided.

The means for providing controlled (i.e. sustained) release of the active ingredient may be selected from any of the known systained-release oral drug delivery systems. Some of the known sustained-release delivery systems for controlling the release of an active ingredient over a course of about four to eight hours includes the wax matrix system, the coated granular system, the "miniature osmotic pump" system and the Forest Synchron system (of Forest Laboratories).

The wax matrix system disperse the active ingredients in a wax binder which slowly dissolves in body fluids to gradually release the active ingredients.

The coated granular system enncapsulates the active ingredients in various polymeric coatings that have varying degrees of solubility depending upon pH and/or enzymes to vary the drug release rate from the respective granules. A multiplicity of granules is filled into a gelatin or similar water-soluble capsule.

In the miniature osmotic "pump," an active ingredient is coated with a semipermeable membrane. The pump works when water-soluble drugs are released through a hole drilled into the membrane.

The preferred controlled-release oral drug delivery system is the Forest Synchron drug delivery system in which the active ingredient MFP is dispersed uniformly and homogeneously throughout a mass of water-swellable modified cellulosic powder or fibers forming a coherent network, as a matrix. The mixture of the fibrous or powdery mass and active ingredients, with optional additives, such as flavoring, binder, lubricant, processing aids and the like, is compacted into a tablet which, prior to use, is hard and dry. After the tabler is swallowed and comes into contact with the aqueous stomach and intestinal fluids, the outer layer of the tablet becomes soft and gelatinous while the inner portions remain dry. At the softened and gelatinous surface, the cellulose powder or fibers become loose and separate from the remaining mass, thereby releasing a portion of the active ingredients. During the period the tablet remains in the stomach and then travels down through the GI tract, the newly exposed outer surfaces become moistened and in turn become soft and gelatinous to loosen additional cellulosic material, thereby allowing additional amounts of MFP and any other dispersed substances to be steadily and generally uniformly released into the stomach or intestines. By the time the tablet has passed through the GI tract, after about four to eight hours, the tablet is completely dissipated and dissolved. Accordingly, the ingested tablet will release a stream of the sodium monofluorophosphate as well as calcium as the other active ingredient.

For further details and discussion of the Forest Synchron drug delivery system, reference is made to the following U.S. patents, the disclosures of which are incorporated hereby by reference thereto: Nos. 3,870,790, 4,226,849, 4,357,469, 4,369,172, 4,389,393 all assigned to Forest Laboratories.

It is one of the important advantages of the present invention that MFP is compatible with calcium compounds, not only the salt of complexing acids, but also water-soluble inorganic calcium compounds, such as $CaCO_3$.

As stated at the outset, any dietary supplement therapy for treatment of or prevention of osteoporosis, alveolar bone disease, and so on, requires relatively large quantities of calcium, usually on the order of about 1000 mg to 2000 mg per day for an average weight adult. According to the present invention, a water-soluble calcium compound is directly incorporated into the sustained-release MFP-containing therapeutic product of this invention.

Thus, according to the preferred embodiment of the invention, the calcium compound is calcium carbonate. Including calcium carbonate in the MFP product not only has the obvious practical advantage or providing the essential fluoride, calcium and phosphate components of bone tissue in a single product, but additionally has the advantage of functioning as an antacid to reduce the gastric pH levels, thereby further alleviating gastric discomfort.

For instance, the following composition provides a practical size tablet:

| | |
|---|---|
| $CaCO_3$ | 625 mg (250 mg Ca) |
| MFP (disodium salt) | 38 mg (5 mg F) |

A regimen of two tablets three times a day will provide a daily dosage of 1500 mg calcium and 30 mg F.

The following list is compiled on the basis of calcium contents, starting with the highest, calcium carbonate, which contains 40% calcium. Thus, 2500 mg of $CaCO_3$ is required to provide 1000 mg supplemental calcium. Analogous figures are provided for seven other calcium compounds.

| Calcium Salt | % Ca | Approximate mg Cpd per 1000 mg Ca |
|---|---|---|
| Ca Carbonate | 40 | 2500 |
| Dicalcium Phosphate | 29 | 3300 |
| Ca Citrate | 24 | 4000 |
| Ca Glycerophosphate | 19 | 5000 |
| Ca Lactate | 18 | 5000 |
| Ca Levulinate | 15 | 7000 |
| Ca Galactogluconate | 10 | 10000 |
| Ca Gluconate | 9.3 | 11000 |

Effectively, any of the above compositions containing calcium can be used to provide about 250 mg of calcium ion in combination with the desired dosage of MFP.

What is claimed is:

1. A medication for providing fluoride ions for the treatment and prevention of bone loss disease, including osteoporosis and alveolar bone loss, which comprises a unitary dosage capsule containing from about 20 to 100 milligrams of sodium monofluorophosphate and of a calcium-containing composition providing 250 mg of calcium ion selected from calcium carbonate, dicalcium phosphate, calcium citrate, calcium glycerophosphate, calcium lactate, calcium levulinate, calcium galactogluconate and calcium gluconate and further containing means for controlling the release of the monofluorophosphate over a period extending from four hours up to eight hours after swallowing, whereby the quantity of fluoride ions at any given time is below the threshold value at which gastric irritation will occur, the means for controlling release of the monofluorophosphate and calcium comprising a hard dry compacted mass of water-swellable powder or fibers of cellulose material forming a coherent network as a matrix in which the monofluorophosphate and calcium are uniformly and homogeneously dispersed, whereby, upon introduction of the unitary dosage into an aqueous medium, the powder or fibers at the surface of the unitary dosage soften and loosen from the remaining mass to thereby release a stream of the monofluorophosphate and calcium.

* * * * *

UNITED STATES PATENT AND TRADEMARK OFFICE
CERTIFICATE OF CORRECTION

PATENT NO. : 4,861,590

DATED : August 29, 1989

INVENTOR(S) : Marcus G. Grodberg, et al

It is certified that error appears in the above-identified patent and that said Letters Patent is hereby corrected as shown below:

On Title page, item [75] Inventor: should read,

Marcus G. Grodberg, Newton, Mass., David J. Baylink, Redlands, Calif.--

Signed and Sealed this

Thirteenth Day of July, 1993

Attest:

MICHAEL K. KIRK

*Attesting Officer*    *Acting Commissioner of Patents and Trademarks*